(12) United States Patent
Taguchi et al.

(10) Patent No.: US 9,610,055 B2
(45) Date of Patent: Apr. 4, 2017

(54) X-RAY CT APPARATUS AND IMAGE PROCESSING APPARATUS

(71) Applicant: TOSHIBA MEDICAL SYSTEMS CORPORATION, Otawara-shi (JP)

(72) Inventors: Hiroki Taguchi, Otawara (JP); John Gulik, Bunkyo (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/789,371

(22) Filed: Jul. 1, 2015

(65) Prior Publication Data
US 2016/0000396 A1 Jan. 7, 2016

(30) Foreign Application Priority Data
Jul. 2, 2014 (JP) ................. 2014-136599

(51) Int. Cl.
*G06K 9/00* (2006.01)
*A61B 6/00* (2006.01)
(Continued)

(52) U.S. Cl.
CPC ............ *A61B 6/5205* (2013.01); *A61B 6/032* (2013.01); *A61B 6/482* (2013.01); *A61B 6/488* (2013.01);
(Continued)

(58) Field of Classification Search
USPC ........ 382/100, 103, 106–107, 128–133, 154, 382/162, 168–193, 209, 219, 224, 232,
(Continued)

(56) References Cited

U.S. PATENT DOCUMENTS

2009/0147919 A1* 6/2009 Goto .................. A61B 6/032
378/86
2009/0262997 A1* 10/2009 Zou .................. G06T 11/005
382/131
(Continued)

FOREIGN PATENT DOCUMENTS

JP 2009-261942 11/2009
JP 2012-081108 4/2012

OTHER PUBLICATIONS

Thorsten R. C. Johnson, et al., "Material differentiation by dual energy CT: initial experience", Eur Radiol, 17, 2007, 8 pages.

*Primary Examiner* — Seyed Azarian
(74) *Attorney, Agent, or Firm* — Oblon, McClelland, Maier & Neustadt, L.L.P.

(57) ABSTRACT

The X-ray CT apparatus includes an X-ray tube, a high-voltage power supply, an X-ray detector and a processing circuitry. The processing circuitry reconstructs, as a first image, any of a monochromatic X-ray image and a polychromatic X-ray image on a basis of pre-reconstruction data acquired by scanning an object, the polychromatic X-ray image being taken in a first X-ray energy band. The processing circuitry reconstructs, as a second image, a polychromatic X-ray image taken in a second X-ray energy band wider than the first X-ray energy band on a basis of a pre-reconstruction data acquired by scanning the object. The processing circuitry identifies an area of a correction target in the first image as a correction area. The processing circuitry corrects the correction area in the second image on a basis of the first image.

18 Claims, 13 Drawing Sheets

(51) Int. Cl.
*G06T 11/00* (2006.01)
*G06T 5/50* (2006.01)
*G06T 11/60* (2006.01)
*G06T 5/00* (2006.01)
*A61B 6/03* (2006.01)
*A61B 6/06* (2006.01)

(52) U.S. Cl.
CPC .......... *A61B 6/5258* (2013.01); *A61B 6/5282* (2013.01); *G06T 5/002* (2013.01); *G06T 5/50* (2013.01); *G06T 11/005* (2013.01); *G06T 11/60* (2013.01); *A61B 6/06* (2013.01); *G06T 2207/10081* (2013.01); *G06T 2211/408* (2013.01)

(58) Field of Classification Search
USPC ....... 382/254, 274–276, 287, 291, 294, 305, 382/312; 378/4, 5, 16, 21, 86
See application file for complete search history.

(56) References Cited

U.S. PATENT DOCUMENTS

| | | | |
|---|---|---|---|
| 2010/0189212 A1* | 7/2010 | Zou | G06T 11/005 378/5 |
| 2012/0236984 A1* | 9/2012 | Chandra | A61B 6/032 378/16 |
| 2014/0363069 A1* | 12/2014 | Hsieh | G06T 5/005 382/131 |

* cited by examiner

X-RAY CT APPARATUS AND IMAGE PROCESSING APPARATUS

CROSS-REFERENCE TO RELATED APPLICATION

This application is based upon and claims the benefit of priority from Japanese Patent Application No. 2014-136599, filed on Jul. 2, 2014, the entire contents of which are incorporated herein by reference.

Further, the contents of Japanese Patent Application No. 2015-130339, filed on Jun. 29, 2015, which claims priority to Japanese Patent Application No. 2014-136599 are also incorporated herein by reference in their entirety.

FIELD

An embodiment as an aspect of the present invention relates to an X-ray CT (computed tomography) apparatus and an image processing apparatus.

BACKGROUND

An X-ray CT apparatus, which provides information on an object as images based on the intensity of X-rays having transmitted through the object, plays an important role in many medical practices including diagnosis and treatment of diseases and surgical planning.

Recent X-ray CT apparatuses use a technique known as dual energy scan. The dual energy scan as referred to herein is a technique for acquiring images by scanning an object using two different types of tube voltages. CT which uses dual energy scan is referred to as "dual energy CT."

Techniques related to the dual energy scan have been known. These techniques can separate materials on the basis of information acquired using two different types of tube voltages, and then acquire various images, such as monochromatic X-ray images (monochromatic images), density images, effective atomic number images, and artifact-free images (images with reduced artifacts). The X-rays used for dual energy scan are polychromatic X-rays (continuous spectrum X-rays) having various X-ray energies and a specific X-ray energy distribution.

Furthermore, techniques have been known that generate two types of polychromatic X-ray images (polychromatic images) that are typical CT images corresponding to respective two types of X-ray energy distributions, and blend both the images, thus generating a monochromatic X-ray image taken at an X-ray energy desired by an operator.

In the monochromatic X-ray images taken at the required X-ray energy through dual energy scanning, beam hardening artifacts are reduced. Unfortunately, the monochromatic X-ray images have a problem of having higher noise than conventional polychromatic X-ray images taken in an X-ray energy band.

In actuality, the conventional polychromatic X-ray images taken at the X-ray energy band have reduced noise. However, these images have a problem in that beam hardening artifacts are difficult to be reduced in comparison with the monochromatic X-ray images.

BRIEF DESCRIPTION OF THE DRAWINGS

In accompanying drawings.

DETAILED DESCRIPTION

Figure 1:
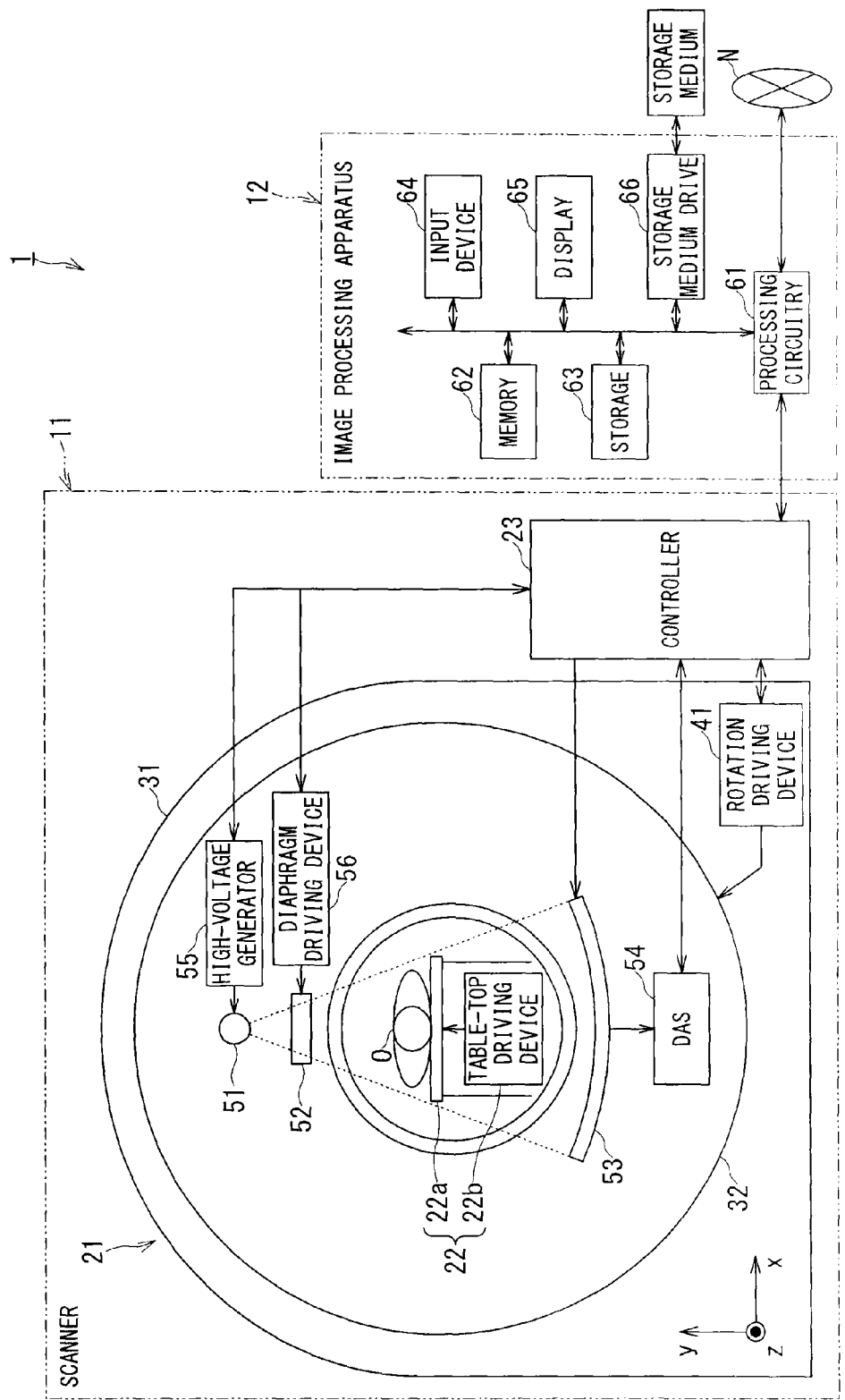
FIG. 1 is a diagram showing a configuration example that represents an X-ray CT apparatus according to a present embodiment.

An X-ray CT apparatus and an image processing apparatus of the present embodiment are described with reference to the accompanying drawings.

To solve the above-described problems, the present embodiment provides the X-ray CT apparatus, including: an X-ray tube configured to emit X-rays; a high-voltage power supply configured to apply a tube voltage to the X-ray tube; an X-ray detector including a plurality of X-ray detection elements, and configured to detect the X-rays; and a processing circuitry configured to: reconstruct, as a first image, any of a monochromatic X-ray image and a polychromatic X-ray image on a basis of pre-reconstruction data acquired by scanning an object, the polychromatic X-ray image being taken in a first X-ray energy band; reconstruct, as a second image, a polychromatic X-ray image taken in a second X-ray energy band wider than the first X-ray energy band on a basis of a pre-reconstruction data acquired by scanning the object; identify an area of a correction target in the first image as a correction area; and correct the correction area in the second image on a basis of the first image.

To solve the above-described problems, the present embodiment provides the X-ray CT apparatus, including: an X-ray tube configured to emit X-rays; a high-voltage power supply configured to apply a tube voltage to the X-ray tube; an X-ray detector including a plurality of X-ray detection elements, and configured to detect the X-rays; and a processing circuitry configured to: generate, as first pre-reconstruction data, any of pre-reconstruction data with monochromatic X-rays, and pre-reconstruction data with polychromatic X-rays on a basis of pre-reconstruction data acquired by scanning an object, the pre-reconstruction data being in a first X-ray energy band; identify a range of a correction target as a correction range in the first pre-reconstruction data on a basis of the first pre-reconstruction data and a second pre-reconstruction data with polychromatic X-rays, the second pre-reconstruction data being acquired by scanning the object and being in a second X-ray energy band wider than the first X-ray energy band; correct the correction range in the second pre-reconstruction data on a basis of the first pre-reconstruction data; and reconstruct a corrected image on a basis of the corrected second pre-reconstruction data.

To solve the above-described problems, the present embodiment provides the image processing apparatus, including: a processing circuitry and a memory, wherein the processing circuitry is configured to: reconstruct, as a first image, any of a monochromatic X-ray image and a polychromatic X-ray image on a basis of pre-reconstruction data acquired by an X-ray detector detecting X-rays having been emitted by an X-ray tube and transmitted through an object, the polychromatic X-ray image being taken in a first X-ray energy band; reconstruct, as a second image, a polychromatic X-ray image taken in a second X-ray energy band wider than the first X-ray energy band on a basis of a pre-reconstruction data; identify an area of a correction target in the first image as a correction area; and correct the correction area in the second image on a basis of the first image.

To solve the above-described problems, the present embodiment provides the image processing apparatus, including: a processing circuitry and a memory, wherein the processing circuitry is configured to: generate, as first pre-reconstruction data, any of pre-reconstruction data with monochromatic X-rays, and pre-reconstruction data with polychromatic X-rays on a basis of pre-reconstruction data acquired by scanning an object with an X-ray CT apparatus, the pre-reconstruction data being in a first X-ray energy band; identify a range of a correction target as a correction range in the first pre-reconstruction data on a basis of the first pre-reconstruction data and a second pre-reconstruction data with polychromatic X-rays, the second pre-reconstruction data being acquired by scanning the object and being in a second X-ray energy band wider than the first X-ray energy band; correct the correction range in the second pre-reconstruction data on a basis of the first pre-reconstruction data; and reconstruct a corrected image on a basis of the corrected second pre-reconstruction data.

Note that the X-ray CT apparatus according to the present embodiment may be any of various types, including a rotate/rotate type in which an X-ray tube and a detector rotate as an integrated unit around an object, and a stationary/rotate type in which many detection elements are arranged to form a ring and only an X-ray tube rotates around the object. The present invention is applicable to any of the types. The present embodiment is described using the case of the rotate/rotate type, which is currently in the mainstream.

The X-ray CT apparatus of the present embodiment is described exemplifying the case of adopting dual energy scan, which is a technique for acquiring images by scanning an object using different types of tube voltages in order to generate images including a monochromatic X-ray image taken at a required X-ray energy, a polychromatic X-ray image taken at in an X-ray energy band, and a polychromatic X-ray blend image, which will be described later. Imaging methods according to the dual energy scan are broadly divided into at least three methods. A first method is a "slow-kV switching method (double rotation method)" that uses a single X-ray tube, and takes an image at a first tube voltage and subsequently takes an image at a second tube voltage different from the first tube voltage. A second method is a "fast-kV switching method (high-speed switching method)" that takes images while rapidly switching the tube voltage of the X-ray tube on a view-by-view basis during rotation (scanning). In this case, a data collector collects data in synchronization with the switching of the tube voltage, thus collecting data items at different tube voltages in a single scan. A third method is a "dual source system (dual tube system)" that includes two X-ray tubes instead of a single X-ray tube, and takes images at different X-ray tube voltages using these tubes. A fourth method is a "multilayer system" that uses X-ray detectors having a multilayered structure. For example, in the case of adopting X-ray detectors (a detector in a shallow layer and a detector in a deep layer) having a two-layer structure, low-energy X-rays are detected by the detector in the shallow layer and high-energy X-rays passing through the detector in the shallow layer are detected by the detector in the deep layer. The present invention is applicable to any of the types. The embodiment is described for the case of the second method.

Alternatively, the present invention may adopt multi-energy scan at least with dual energy (double energy).

Alternatively, the present invention may adopt a photon counting X-ray CT apparatus, collect pre-reconstruction data based on single energy scan, and discriminate energies, thereby generating a monochromatic X-ray image taken at a required energy.

FIG. 1 is a diagram showing a configuration example that represents an X-ray CT apparatus according to a present embodiment.

FIG. 1 shows an X-ray CT apparatus 1 that executes dual energy scan according to the present embodiment. The X-ray CT apparatus 1 mainly includes a scanner 11 and an image processing apparatus (console) 12. The scanner 11 of the X-ray CT apparatus 1 is typically installed in an examination room and used to generate X-ray transmission data on a patient O (object). On the other hand, the image processing apparatus 12 is typically installed in a control room next to the examination room, and is configured to generate projection data based on the transmission data and generate and display a reconstructed image.

The scanner 11 of the X-ray CT apparatus 1 includes a gantry 21, a bed device 22, and a controller (processing circuit) 23.

The gantry 21 of the scanner 11 includes a stationary part 31 fixed onto a base (not shown), and a rotational part 32.

The stationary part 31 includes a rotation driving device 41. The rotation driving device 41 has a mechanism that is controlled by a controller 23 to rotate the rotational part 32 with respect to the stationary part 31 such that the rotational part 32 rotates around an opening including the center of rotation while maintaining the positional relationship.

The rotational part 32 integrally holds an X-ray source (X-ray tube) 51, a diaphragm 52, an X-ray detector 53, a DAS (data acquisition system) 54, a high-voltage generator 55, and a diaphragm driving device 56. The rotational part 32 has a configuration that can rotate the X-ray tube 51, the diaphragm 52, the X-ray detector 53, the DAS 54, the high-voltage generator 55, and the diaphragm driving device 56 in an integrated manner around the patient O in a state where the X-ray tube 51 is opposed to the X-ray detector 53. A direction parallel to the rotation center axis of rotational part 32 is referred to as a z-axis direction. A plane orthogonal to the z-axis direction is defined by an x-axis direction and a y-axis direction.

The X-ray tube 51 generates X-rays (continuous spectrum X-rays) by bombarding a metal target with an electron beam at a tube voltage supplied from the high-voltage generator 55 and emits the X-rays toward the X-ray detector 53. An X-ray fan beam or an X-ray cone beam is formed from the X-rays emitted from the X-ray tube 51. An electric power necessary for X-ray irradiation is supplied to the X-ray tube 51 according to control of the controller 23 through the high-voltage generator 55.

The diaphragm 52 is driven by the diaphragm driving device 56 to adjust an irradiation range (irradiation field) of X-rays emitted from the X-ray tube 51. That is, the diaphragm driving device 56 adjusts the opening the diaphragm 52, thereby allowing the X-ray irradiation range to be changed in the slice direction.

The X-ray detector 53 is a one-dimensional array detector including multiple detection elements that are arranged in a channel direction and residing on a single column (slice). Alternatively, the X-ray detector 53 may be a two-dimensional array detector (also referred to as a multi-slice detector) that includes detection elements arranged in a matrix, that is, multiple detection elements in each of the channel direction and the slice direction. In the case where the X-ray detector 53 is the multislice detector, scanning in one rotation can take an image of a three-dimensional imaging area having a width in the column direction (volume scan). The X-ray detector 53 detects X-rays emitted from the X-ray tube 51 under control of the controller 23.

The DAS 54 collects data in synchronization with switching of the tube voltage during dual energy scan. The DAS 54 amplifies a signal of the transmission data (X-ray detection data) detected by each detecting element of the X-ray detector 53 and converts the signal into a digital signal. Output data of the DAS 54 is supplied to the image processing apparatus 12 via the controller 23 of the scanner 11. Details of the DAS 54 are described later.

The high-voltage generator 55 supplies the X-ray tube 51 with an electric power required to execute dual energy scan under control of the controller 23.

Figure 2:
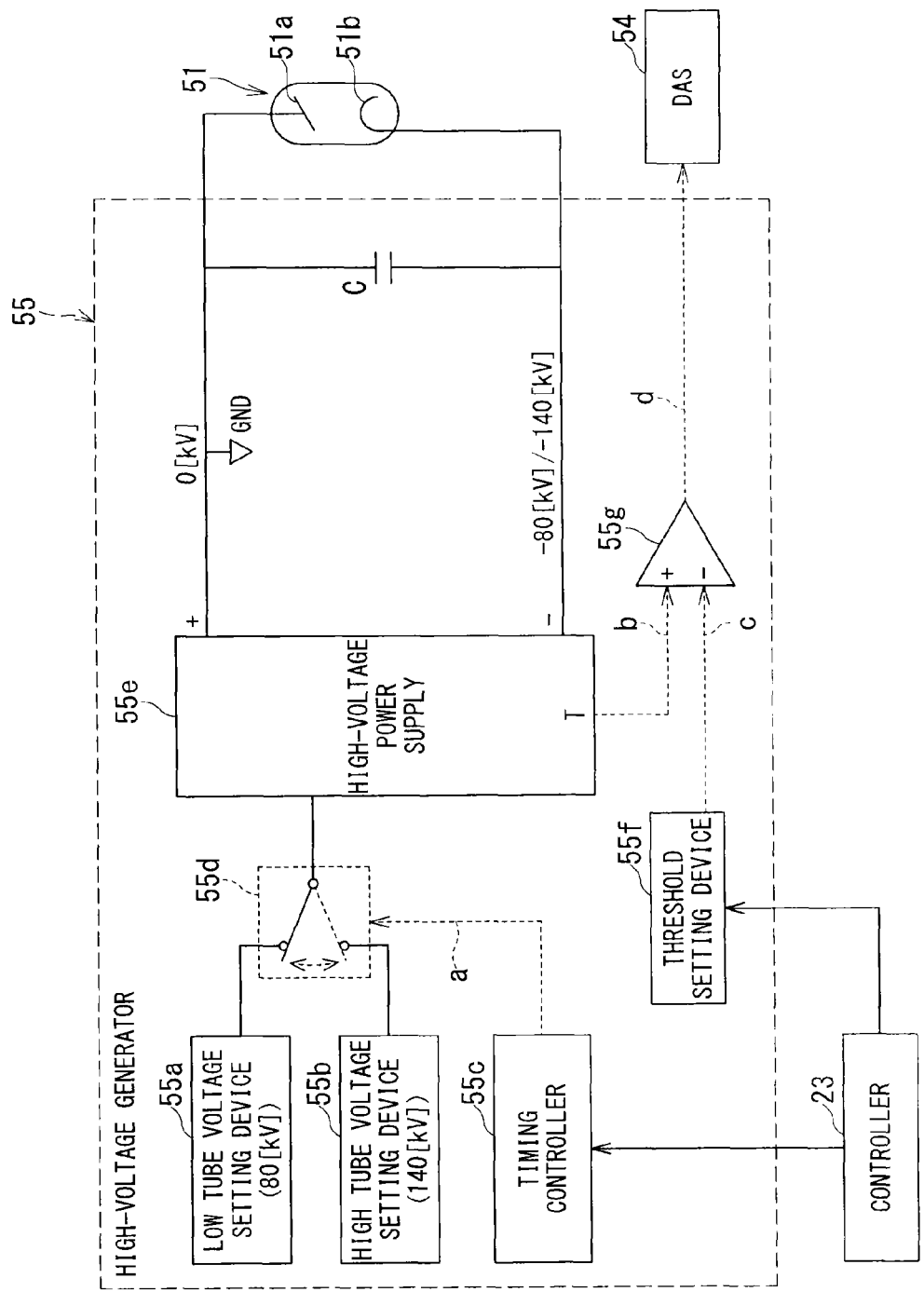
FIG. 2 is a diagram showing a configuration example of an X-ray tube and a high-voltage generator, which are included in the X-ray CT apparatus according to the present embodiment.

FIG. 2 is a diagram showing a configuration example of the X-ray tube 51 and the high-voltage generator 55, which are included in the X-ray CT apparatus 1 according to the present embodiment.

As shown in FIG. 2, the X-ray tube 51 includes an anode 51a and a filament (cathode) 51b. The high-voltage generator 55 includes a low tube voltage setting device 55a, a high tube voltage setting device 55b, a timing controller 55c, a switch 55d, a high-voltage power supply 55e, a threshold setting device 55f, a comparator 55g, and a capacitor C. The case is hereinafter described where high-kV (high tube voltage) is 140 kV and low-kV (low tube voltage) is 80 kV in dual energy scan. However, this is not restrictive, and any combination of a high tube voltage and a low tube voltage may be used. In dual energy scan, high-kV (high tube voltage) is defined as a "first tube voltage" and low-kV (low tube voltage) is defined as a "second tube voltage."

The low tube voltage setting device 55a sets low-kV while the high tube voltage setting device 55b sets high-kV. Output of each of the tube voltage setting devices 55a and 55b can be selected. The output of the tube voltage setting device 55a or 55b is connected to the high-voltage power supply 55e via the switch 55d controlled by the timing controller 55c. The switch 55d is controlled by a signal "a" output from the timing controller 55c. The low tube voltage setting device 55a is selected when the signal "a" indicates "L," while the high tube voltage setting device 55b is selected when the signal "a" indicates "H."

A positive output of the high-voltage power supply 55e is electrically connected to the anode 51a of the X-ray tube 51 and grounded. Meanwhile, a negative output of the high-voltage power supply 55e is electrically connected to the filament 51b of the X-ray tube 51. The output of the high-voltage power supply 55e is switched to low-kV or high-kV (e.g., the tube voltage of 80 or 140 kV) at a timing of switching according to the signal "a." The high-voltage power supply 55e is equipped with a tube voltage detecting terminal T, which is connected to a positive input of the comparator 55g. The threshold setting device 55f is connected to a negative input of the comparator 55g.

The comparator 55g receives input of a signal "b" from the tube voltage detecting terminal T of the high-voltage power supply 55e and input of a signal "c" from the threshold setting device 55f, and outputs, to the DAS 54, a signal "d" indicating "L" when the signal "b" is larger than the signal "c" or indicating "H" when the signal "b" is equal to or smaller than the signal "c." When the signal "d" indicates "L," the DAS 54 determines that the data is transmission data at low-kV. When the signal "d" indicates "H," the DAS 54 determines that the data is transmission data at high-kV.

The controller 23 performs, in accordance with a tube voltage control signal from a tube voltage controlling 71 of a processing circuitry 61 described later with reference to FIG. 4, dual energy scan by controlling switching of the switch 55d via the timing controller 55c of the high-voltage generator 55 and selects whether to cause the high-voltage power supply 55e to output low-kV set by the low tube voltage setting device 55a or output high-kV set by the high tube voltage setting device 55b. In response to a control signal from the controller 23, the switch 55d provides the high-voltage power supply 55e with the selected tube voltage setting signal.

The control signal from the controller 23 is also sent to the DAS 54. The DAS 54 recognizes whether data collected by dual energy scan is produced by low-kV X-ray irradiation or high-kV X-ray irradiation.

Returning to the description of FIG. 1, the diaphragm driving device 56 has a mechanism for adjusting the X-ray irradiation range in the X-ray slice direction in the diaphragm 52 under the control of the controller 23.

The bed device 22 of the scanner 11 includes a table-top 22a and a table-top driving device 22b. The patient O can lie on the table-top 22a.

The table-top driving device 22b has a mechanism that raises and lowers the table-top 22a along the y-axis direction under control of the controller 23 while advancing and retracting the table-top 22a along the z-axis direction. The table-top driving device 22b inserts the patient O lying on the table-top 22a into the opening including the center of rotation of the rotational part 32, and retracts the patient O lying on the table-top 22a from the opening.

The controller 23 of the scanner 11 includes a CPU (central processing unit), which is a processing circuit and is not shown, and a memory. The controller 23 controls the rotation driving device 41, the X-ray detector 53, the DAS 54, the high-voltage generator 55 and the diaphragm driving device 56 of the gantry 21, and the table-top driving device 22b of the bed device 22, according to an instruction from the image processing apparatus 12, to perform dual energy scan.

The image processing apparatus 12 of the X-ray CT apparatus 1 is configured based on a computer and is capable of intercommunicating with a network (local area network) N. The image processing apparatus 12 is mainly composed of basic hardware, including the processing circuitry 61, a memory 62, a storage 63, an input device 64, and a display 65. The processing circuitry 61 is interconnected with each of the hardware configuration elements configuring the image processing apparatus 12 via a bus serving as a common signal transmission path. In some cases, the image processing apparatus 12 includes a storage medium drive 66.

The processing circuitry 61 means any of dedicated and general-purpose CPUs (central processing units), an application specific integrated circuit (ASIC), and a programmable logic device. The programmable logic device may be, for example, any of a simple programmable logic device (SPLD), a complex programmable logic device (CPLD), and a field programmable gate array (FPGA). The processing circuitry 61 achieves the functions shown in FIGS. 4 and 5 by reading and executing programs stored in the memory 62 or directly implemented in the processing circuitry 61.

Furthermore, the processing circuitry 61 may be configured by a single-piece processing circuitry, or an integrated processor circuitry including multiple independent processing circuitries. In the latter situation, memories 62 for recording programs may be separately provided for the respective processing circuitries. Alternatively, one memory 62 may store programs corresponding to the respective functions of circuitries (processing circuitry).

The memory 62 is a storage device including a ROM (read only memory) and a RAM (random access memory). The memory 62 is for IPL (initial program loading) and BIOS (basic input/output system) and stores data, and is used as a working memory of the processing circuitry 61 and to temporarily store data.

The storage 63 includes a memory and an HDD (hard disc drive). The storage 63 stores data required to execute a control program used by the processing circuitry 61, data received via an interface (not shown) or removable media, and data generated by the processing circuitry 61.

The storage 63 stores programs (including not only application programs but also an OS (operating system)) installed in the image processing apparatus 12, and data. The OS may also provide a GUI (graphical user interface), which uses a lot of graphics to display information on the display 65 for an operator, such as a practitioner, and allows basic operations to be performed through the input device 64.

The input device 64 is a pointing device allowing the operator to operate. An input signal according to an operation is sent to the processing circuitry 61.

The display 65 includes an image combining circuit, a VRAM (video random access memory), a display, and the like which are not shown. The image combining circuit generates combined data where image data is combined with character data indicating various parameters. The VRAM deploys the combined data on the display. The display may be a liquid crystal display, CRT (cathode ray tube) or the like, and sequentially displays images.

Figure 3:
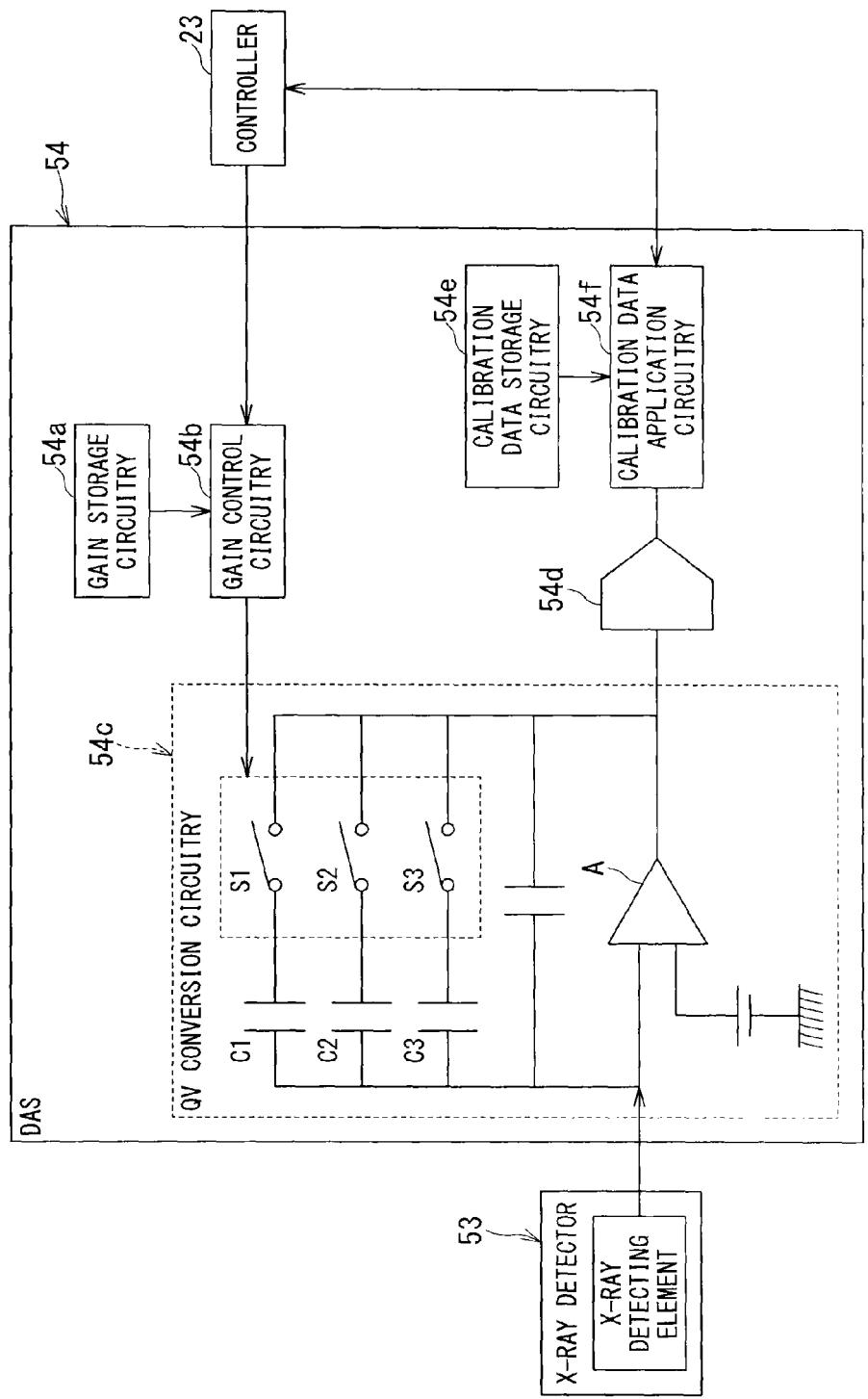
FIG. 3 is a diagram showing a configuration example of a DAS installed in the X-ray CT apparatus according to the present embodiment.

FIG. 3 is a diagram showing a configuration example of the DAS 54 installed in the X-ray CT apparatus 1 according to the present embodiment.

As shown in FIG. 3, the DAS 54 includes a gain storage circuitry 54a, a gain control circuitry 54b, a QV conversion circuitry (integrating circuit and gain variable amplifier circuit) 54c, an A/D conversion circuitry 54d, a calibration data storage circuitry 54e, and a calibration data application circuitry 54f. It is assumed hereinafter that the circuits 54a to 54f are provided for each of X-ray detecting elements configuring the X-ray detector 53. Alternatively, these circuits may be provided for each X-ray detecting element group that includes multiple X-ray detecting elements.

The gain storage circuitry 54a preliminarily stores gains (amplification factors). The gain storage circuitry 54a preliminarily stores a gain corresponding to the size of a head for cephalography, a gain corresponding to the size of a chest for thoracic radiography, and a gain corresponding to the size of an abdomen for abdominal radiography. The gain storage circuitry 54a may also store gains that allow images of multiple portions having different body diameters to be taken by irradiation with X-rays only one time.

The gain control circuitry 54b controls, under control of the controller 23, the QV conversion circuitry 54c to set the gain stored in the gain storage circuitry 54a.

The QV conversion circuitry 54c periodically integrates, in synchronization with an X-ray irradiation period, a voltage signal output from an X-ray detection element $E_{m,n}$ in an n-th column on an m-th channel of the X-ray detector 53. Furthermore, the QV conversion circuitry 54c includes an operational amplifier A, three capacitors C (C1, C2 and C3) having different capacitances, and three switches S (S1, S2 and S3). The switches S1, S2 and S3 are associated with the capacitors C1, C2 and C3, respectively, and on-off controlled by the gain control circuitry 54b. The QV conversion circuitry 54c can set six gains through on-off combinations of the capacitors C1, C2 and C3. Alternatively, the QV conversion circuitry 54c may include six capacitors C having the same capacitance in order to set six gains. The number of capacitors C included in the QV conversion circuitry 54c is not limited to three or six.

The QV conversion circuitry 54c amplifies transmission data output from the X-ray detection element $E_{m,n}$ using the gain controlled by the gain control circuitry 54b.

The A/D conversion circuitry 54d converts analog data output from the QV conversion circuitry 54c into digital data.

The calibration data storage circuitry 54e stores correct calibration data preliminarily acquired as data for calibration through dual energy scan under the control of the controller 23. The calibration data stored in the calibration data storage circuitry 54e is described.

The calibration data application circuitry 54f applies calibration data stored in the calibration data storage circuitry 54e to output data of the A/D conversion circuitry 54d produced as a result of dual energy scan. The calibration data application circuitry 54f recognizes a tube voltage pair of data items collected through dual energy scan, and values of tube current in tube current modulation. The calibration data application circuitry 54f acquires calibration data items corresponding to the recognized tube voltage pair and the values of tube current from the calibration data storage circuitry 54e, and applies the data items to an output signal of the A/D conversion circuitry 54d.

The calibration data application circuitry 54f interpolates, when the calibration data storage circuitry 54e has the calibration data items for discrete tube currents, the calibration data items, and applies the interpolation to absence of data on tube current.

Returning to the description of FIG. 1, the image processing apparatus 12 applies a logarithmic conversion process or a correction process (pre-processing), such as sensitivity correction, to raw data input from the DAS 54 of the scanner 11 to thereby generate projection data, and stores the projection data in the storage 63. Furthermore, the image processing apparatus 12 performs a process of removing scattered rays from the pre-processed projection data. The image processing apparatus 12 removes the scattered rays on the basis of the values of the projection data in an X-ray exposure range, and performs scattered ray correction by subtracting the scattered rays estimated from the magnitude of value of projection data to be subjected to scattered ray correction or projection data adjacent thereto. The image processing apparatus 12 generates image data on the basis of the corrected projection data, and stores the image data in the storage 63 or displays the image data on the display 65.

Figure 4:
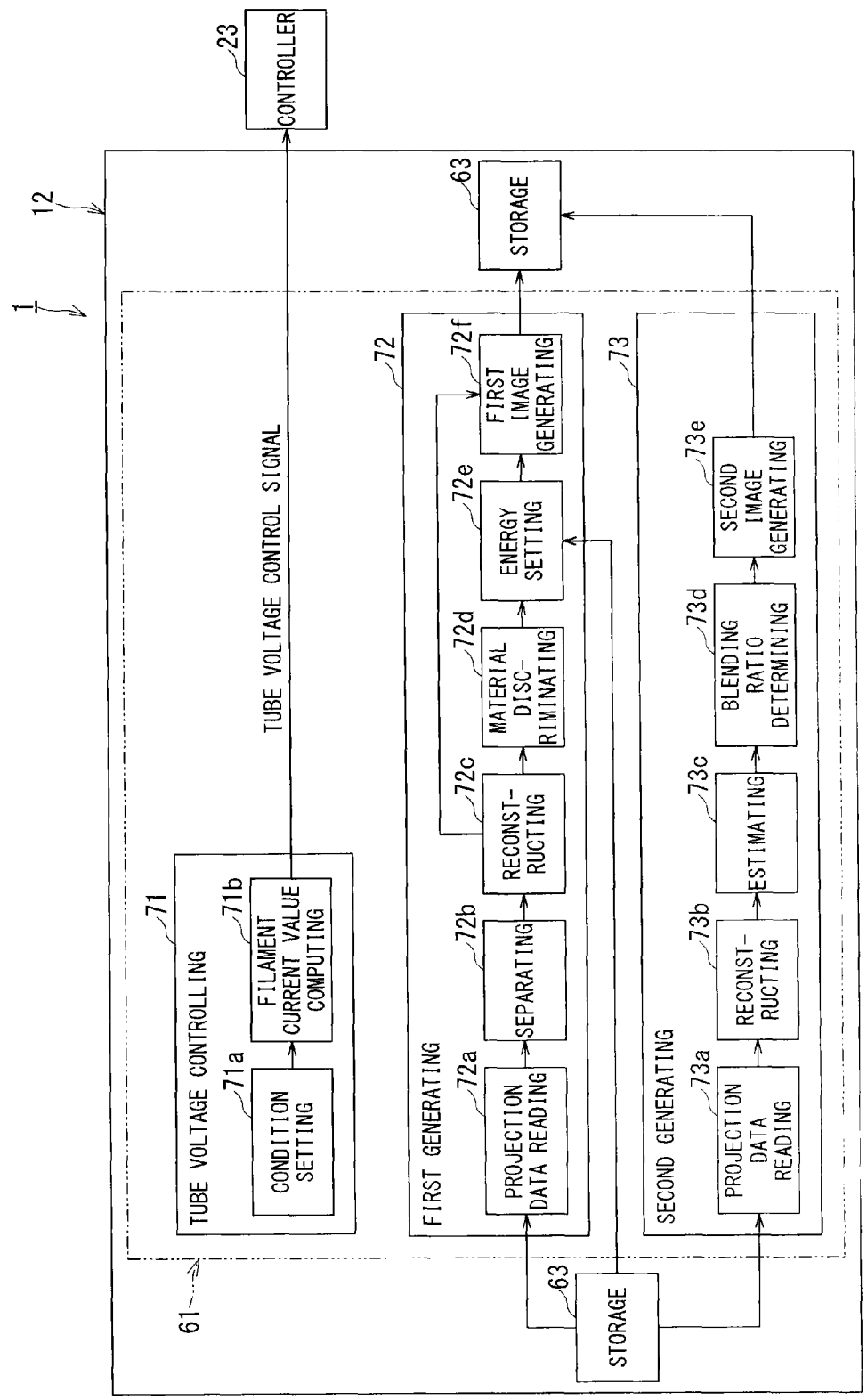
FIGS. 4 and 5 are block diagrams showing functions of the X-ray CT apparatus according to the present embodiment.
Figure 5:
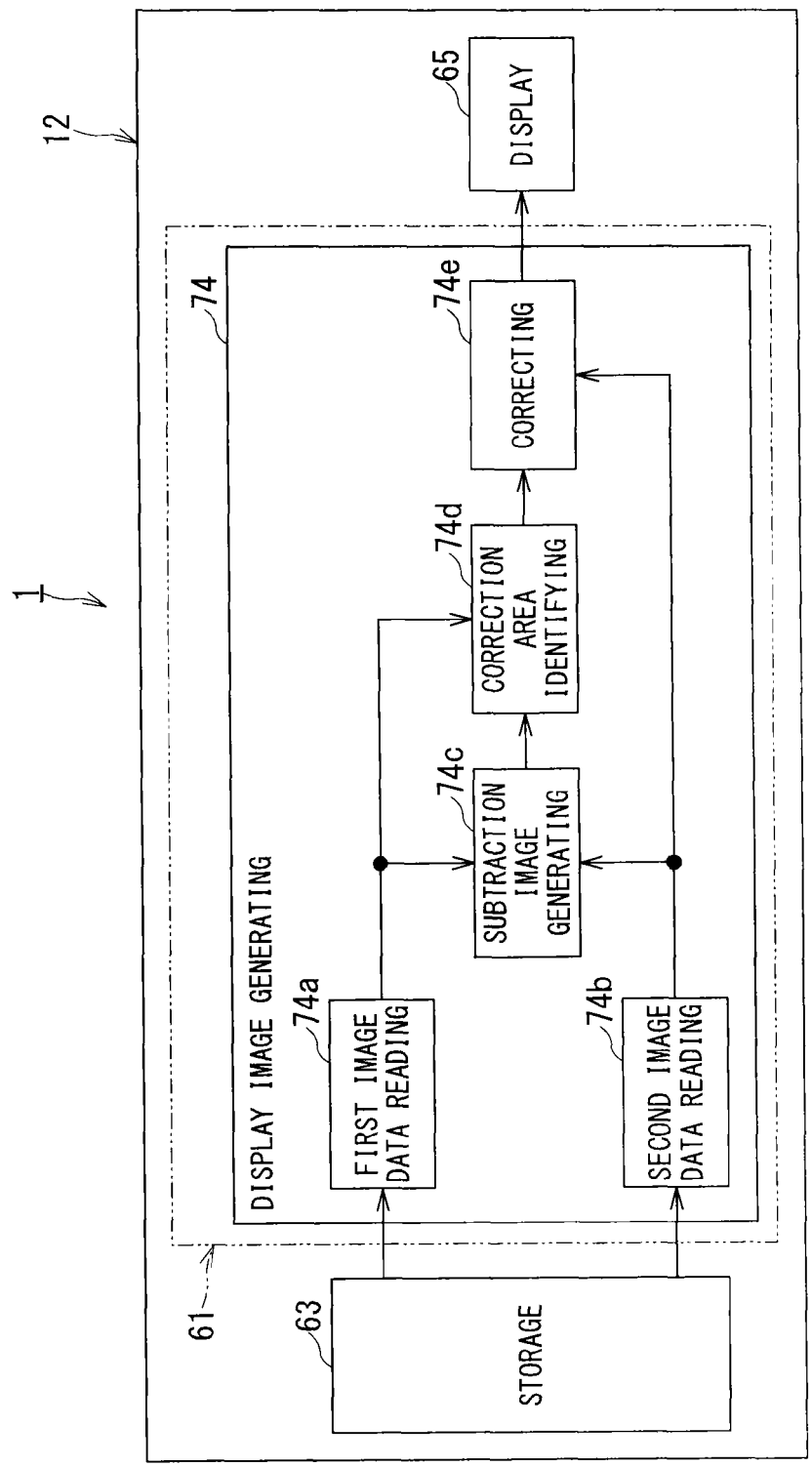

FIGS. 4 and 5 are block diagrams showing the functions of the X-ray CT apparatus 1 according to the present embodiment.

The processing circuitry 61 of the image processing apparatus 12 executes programs, thereby allowing the X-ray CT apparatus 1 to function as a tube voltage controlling 71, a first generating 72, a second generating 73, and a display image generating 74 as shown in FIGS. 4 and 5. All or some of the functions 71 to 74 may be provided not only for the image processing apparatus 12 but also for the high-voltage generator 55 and the controller 23.

The functions 71 to 74 are configured as respective programs, which allow a single processing circuit to execute the functions 71 to 74. Alternatively, the functions 71 to 74 may be implemented in respective dedicated program executing circuits, which are independent from each other.

First, the tube voltage controlling 71 shown in FIG. 4 is described.

The tube voltage controlling 71 has functions that generate a tube voltage control signal for controlling switching of the tube voltage generated by the high-voltage generator 55 and conditions and the like at a time of switching, and supply the controller 23 with the generated tube voltage control signal. More specifically, the tube voltage controlling 71 functions as a condition setting 71a and a filament current value computing 71b.

The condition setting 71a sets a tube current condition (the maximum tube current value during modulation) on the basis of a scan plan, information acquired from a positioning image before scanning (scout image), or data on X-rays having transmitted through the object during scanning. Furthermore, the condition setting 71a sets the condition of modulation of the amount of X-ray irradiation with respect to the time series on the basis of the scanning plan, the information acquired from the scout image, or the data on X-rays having transmitted through the object during scanning.

Examples of the modulation include periodic modulation (rotation angle modulation) with respect to the rotation angle, modulation (z-axis modulation) in z-axis direction, periodic modulation (electrocardiograph-synchronized modulation) in synchronization with an electrocardiographic signal, and modulation (highly sensitive portion modulation) for reducing radiation exposure of highly sensitive portions, such as eyeballs and an ovary, and combinations thereof. The tube current condition and modulation condition set by the condition setting 71a are sent to the filament current value computing 71b.

The filament current value computing 71b computes the filament current value of the X-ray tube 51 based on the tube current condition and the modulation condition set by the condition setting 71a through the controller 23 and the high-voltage generator 55. Furthermore, the filament current value computing 71b supplies the computed filament current value to the filament of the X-ray tube 51.

Next, the first generating 72 shown in FIG. 4 is described.

The first generating 72 has a function of generating (reconstructing), as a first image, a monochromatic X-ray image taken at an appropriate X-ray energy, on the basis of a pre-reconstruction data set (pre-reconstruction data from multiple views) acquired by dual energy scan. Alternatively, the first generating 72 has a function of generating, as the first image, a polychromatic X-ray image taken in a relatively narrow X-ray energy band (an X-ray energy band narrower than the X-ray energy band of the polychromatic X-ray image by the second generating 73, which will be described later) on the basis of the pre-reconstruction data set acquired by dual energy scan. The present embodiment is described exemplifying the case where the first generating 72 generates, as a first image, the monochromatic X-ray image taken at an appropriate X-ray energy.

Figure 6:
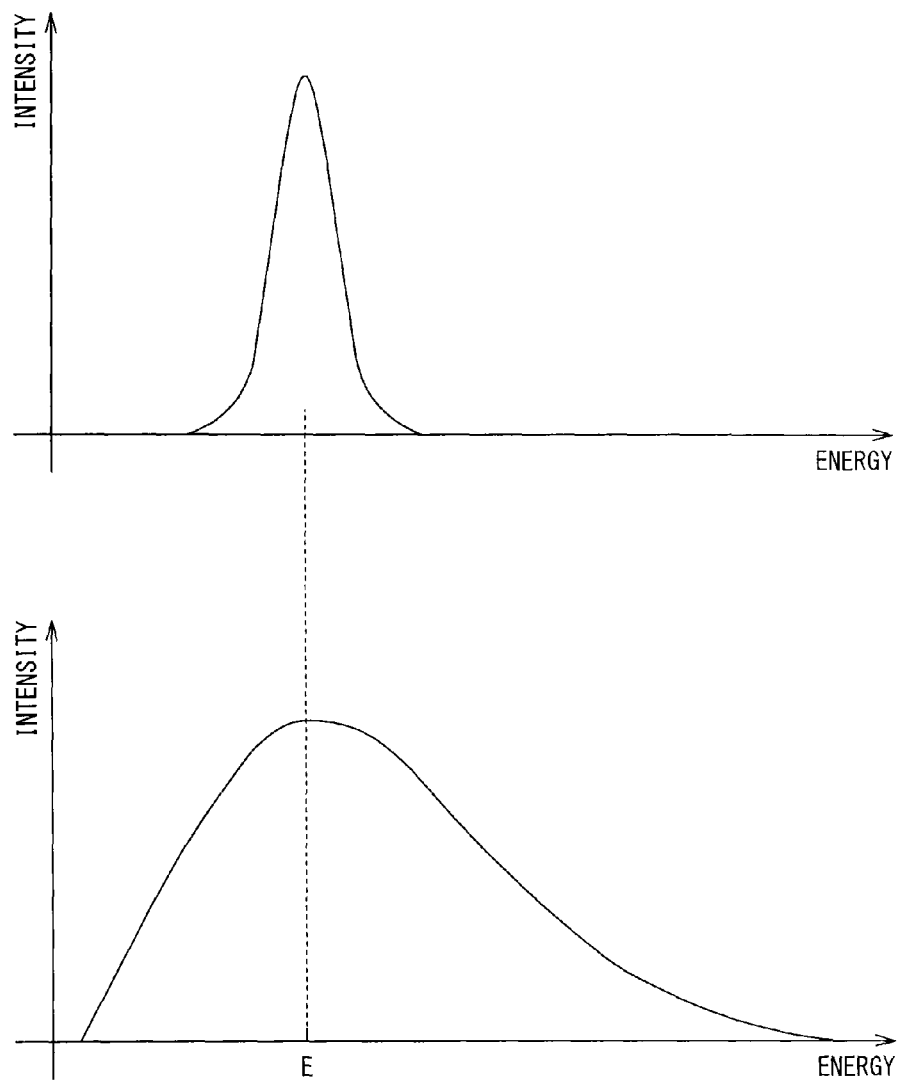
FIG. 6 is a diagram showing a relatively narrow X-ray energy band according to a first image taking.

FIG. 6 is a diagram showing a relatively narrow X-ray energy band according to a first image taking.

The upper part of FIG. 6 shows a spectrum illustrating the X-ray energy according to the first image taking. The lower part of FIG. 6 shows a spectrum illustrating the X-ray energy according to a second image taking, which will be described later.

As shown in FIG. 6, the X-ray energy band according to the first image taking is narrower than the X-ray energy band according to the second image taking. Furthermore, as shown in FIG. 6, the X-ray energy band according to the first image taking includes an effective energy E of the X-ray energy band according to the second image taking.

Returning to the description of FIG. 4, the pre-reconstruction data used by the first generating 72 is sometimes raw data, and is sometimes projection data. If the pre-reconstruction data is raw data, the pre-reconstruction data set is a raw data set (raw data from multiple views). If the pre-reconstruction data is projection data, the pre-reconstruction data set is a projection data set (projection data from multiple views). Multiple views (projection angle) are sometimes an angle within one rotation of the rotational part 32 (shown in FIG. 1), and is sometimes an angle within half a rotation plus α. The present embodiment is described exemplifying the case where the pre-reconstruction data is projection data.

The X-ray CT apparatus 1 executes dual energy scan and collects a projection data set based on each scan. For example, the "fast-kV switching method (high-speed switching method)" that rapidly switches the tube voltage of the X-ray tube and takes an image for each view during rotation (scanning) is used as a method of dual energy scan.

The first generating 72 functions as a projection data reading 72a, a separating 72b, a reconstructing 72c, a material discriminating 72d, an energy setting 72e and a first image generating 72f.

The projection data reading 72a reads two types of projection data sets based on two types of tube voltages stored in the storage 63 of the image processing apparatus 12.

The separating 72b separates (discriminates) predefined reference materials (water, contrast material, $CaCo_3$, uric acid, fat and the like) existing in a radiographic coverage using two types of projection data sets from the projection data reading 72a. The separating 72b then separates the two reference materials, and generates two types of monochromatic X-ray projection data sets corresponding to the respective two reference materials. The present embodiment is described for the case where the separating 72b separates the two reference materials, and generates the two types of monochromatic X-ray projection data sets corresponding to the respective two reference materials. However, the reference materials are not limited to two. Alternatively, any plurality of materials may be adopted.

The reconstructing 72c reconstructs a reference material image (reference material weighted image) as image data on the basis of the two types of monochromatic X-ray projection data sets separated by the separating 72b. The reconstructing 72c generates a reference material image of a reference material 1 on the basis of the projection data set of the reference material 1, and generates a reference material image of a reference material 2 on the basis of the projection data set of the reference material 2. For example, the reconstructing 72*c* generates a reference material image of the water component on the basis of the projection data set where a water component is weighted, and generates a reference material image of a contrast material component on the basis of the projection data set where a contrast material component is weighted.

The multiple reference material images generated by the reconstructing 72*c* can be added together while changing the weighting coefficient to generate multiple monochromatic X-ray images corresponding to the respective X-ray energies.

The material discriminating 72*d* discriminates (identifies) each material (including tissue, contrast material, bones and the like) existing in the radiographic coverage using two types of reference material images generated by the reconstructing 72*c*. The concepts of a method of separating the reference materials existing in the radiographic coverage and a method of discriminating the materials are herein described.

The methods of identifying the materials according to dual-energy based data are roughly divided into a technique that identifies the material on the basis of the image itself generated from the two types of projection data sets, and a technique that separates the two types of reference materials on the basis of the two types of projection data sets, generates reference material images based on the respective reference materials, and identifies the materials from the respective reference material images. Although the present invention is applicable to each case, the present embodiment is described exemplifying the latter. It is a matter of course that a method other than the above examples may be adopted only if the method can identify the materials.

The energy setting 72*e* refers to the energy table preliminarily stored in the storage 63 on the basis of a discrimination result from the material discriminating 72*d*, and sets the X-ray energy (or a relatively narrow X-ray energy band) for generating the monochromatic X-ray image pertaining to each material existing in the radiographic coverage.

The first image generating 72*f* generates, as a first image, the monochromatic X-ray image (or a polychromatic X-ray image taken at the relatively narrow X-ray energy band) taken at an appropriate X-ray energy for each material on the basis of the X-ray energy on each material set by the energy setting 72*e* and images of two reference materials generated by the reconstructing 72*c*.

The first image generating 72*f* stores, as the first image, the monochromatic X-ray image (or a polychromatic. X-ray image taken at the relatively narrow X-ray energy band), in the storage 63. The "monochromatic X-ray image" used in the present embodiment is an image based on the projection data set acquired using the continuous spectrum X-rays having a specific X-ray effective energy, and means an image having a relationship that is equivalent to an image acquired in the case of imaging using the monochromatic X-ray having a specific X-ray energy.

Next, the second generating 73 shown in FIG. 4 is described.

The second generating 73 has a function that generates (reconstructs), as a second image, a polychromatic X-ray image taken in a relatively wide X-ray energy band (an X-ray energy band wider than the X-ray energy band for the polychromatic X-ray image by the first generating 72) from the pre-reconstruction data set based on single energy scan. In a first case, the second generating 73 generates, as the second image, a polychromatic X-ray image taken at the relatively wide X-ray energy band, from the projection data set based on single energy scan.

In a second case, the second generating 73 generates, as the second image, a polychromatic X-ray image taken at the relatively wide X-ray energy band from the projection data set based on one mode of the dual energy scan. In a third case, two types of polychromatic X-ray images are generated from two types of projection data sets based on the dual energy scan, the two types of polychromatic X-ray images are blended together, and a simulated polychromatic X-ray image (hereinafter, referred to as a "polychromatic X-ray blend image") taken at the relatively wide X-ray energy band is generated as the second image.

In the second and third cases, the X-ray CT apparatus 1 executes the dual energy scan, and collects the two types of projection data sets. For example, the "fast-kV switching method (high-speed switching method)" that rapidly switches the tube voltage of the X-ray tube and takes an image for each view during rotation (scanning) is used as one method of the dual energy scan.

In the case of using the polychromatic X-ray blend image as the second image (the third case), the method of generating the polychromatic X-ray blend image is according to Patent Document, Japanese Patent Application Publication (Laid-open: KOKAI) No. 2012-81108 A). That is, in the case of using the polychromatic X-ray blend image as the second image, the second generating 73 includes a projection data reading 73*a*, a reconstructing 73*b*, an estimating 73*c*, a blending ratio determining 73*d*, and a second image generating 73*e*.

The projection data reading 73*a* reads the two types of projection data sets stored in the storage 63 of the image processing apparatus 12.

The reconstructing 73*b* uses the two types of projection data sets from the projection data reading 73*a* to generate a first polychromatic X-ray image taken in a first X-ray energy band from the projection data set based on the first mode of the dual energy scan, and a second polychromatic X-ray image taken in a second X-ray energy band from the projection data set based on the second mode of the scan.

The estimating 73*c* estimates abundance ratio of one of the first and second materials to the other for each pixel on the basis of the pixel values of the first polychromatic X-ray image and the second polychromatic X-ray image that are generated by the reconstructing 73*b*.

The blending ratio determining 73*d* determines the blending ratio between the pixel values of the first polychromatic X-ray image and the second polychromatic X-ray image for each pixel on the basis of the abundance ratio between the first and second materials for each pixel estimated by the estimating 73*c* and the reduction ratio of the attenuation coefficients of the first and second materials. The reduction ratios of the attenuation coefficients of the first and second materials are indicators that indicate reduction from the attenuation coefficients of the first and second materials pertaining to the first X-ray energy band or the second X-ray energy band to the attenuation coefficients of the first and second materials pertaining to the above-described relatively wide X-ray energy band.

The second image generating 73*e* blends the first polychromatic X-ray image with the second polychromatic X-ray image according to the blending ratio determined by the blending ratio determining 73*d*, thereby generating, as the second image, the polychromatic X-ray blend image taken in the above-described relatively wide X-ray energy band. The second image generating 73*e* stores the polychromatic X-ray blend image in the storage 63.

Figure 7:
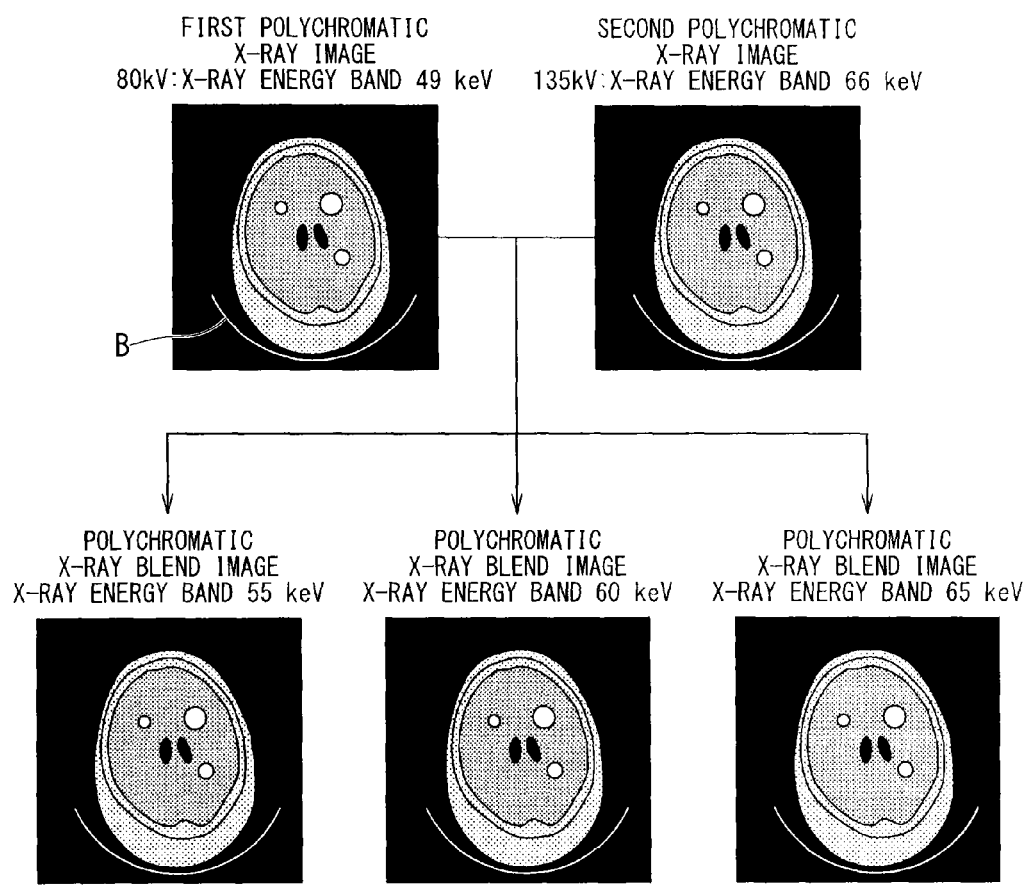
FIG. 7 is a diagram showing generation of polychromatic X-ray blend images.

FIG. 7 is a diagram showing generation of the polychromatic X-ray blend images.

The upper part of FIG. 7 shows the first polychromatic X-ray image taken in the first X-ray energy band (around 49 keV) from the projection data set based on the first mode of scan (tube voltage: 80 kV) of the dual energy scan, and the second polychromatic X-ray image taken in the second X-ray energy band (around 66 keV) from the projection data set based on the second mode of scan (tube voltage: 135 kV). On the other hand, the lower part of FIG. 7 shows three polychromatic X-ray blend images taken in respective three types of X-ray energy bands (around 55, 60 and 65 keV) generated on the basis of two types of polychromatic X-ray images. A beam hardening artifact B exists in each of the polychromatic X-ray images and polychromatic X-ray blend images.

Next, the display image generating 74 shown in FIG. 5 is described.

The display image generating 74 generates a display image, which is to be displayed, on the basis of the first image generated by the first generating 72 and the second image generated by the second generating 73. The display image generating 74 includes a first image data reading 74a, a second image data reading 74b, a subtraction image generating 74c, a correction area identifying 74d, and a correcting 74e.

The second image generated by the second generating 73 is any of the polychromatic X-ray image from the projection data set based on the single energy scan, the polychromatic X-ray image from the projection data set based on one mode of the dual energy scan, and the polychromatic X-ray blend image where polychromatic X-ray images from the projection data sets based on the respective modes of the dual energy scan are blended (the lower part of FIG. 7).

The first image data reading 74a reads the first image that is generated by the first generating 72 and stored in the storage 63 of the image processing apparatus 12.

The second image data reading 74b reads the second image that is generated by the second generating 73 and stored in the storage 63 of the image processing apparatus 12.

The subtraction image generating 74c performs subtraction between the first image read by the first image data reading 74a and the second image read by the second image data reading 74b, thereby generating a subtraction image. If the second image is the polychromatic X-ray blend image, it is preferred that the subtraction image generating 74c perform subtraction using the first image and the second image having CT values (average values) substantially identical (closest) to each other. In this case, the first image at the X-ray energy having a CT value substantially identical to that of the second image is selected, or the second image in the X-ray energy band having a CT value substantially identical to that of the first image is selected.

The X-ray energies (X-ray energy bands) of the selected first and second images may be set in advance such that the first image and the second image subjected to subtraction have CT values substantially identical to each other. Alternatively, the first and second images having the same X-ray energy may be generated. The amount of beam hardening on the image can be computed from the subtraction by the subtraction image generating 74c.

Figure 8:
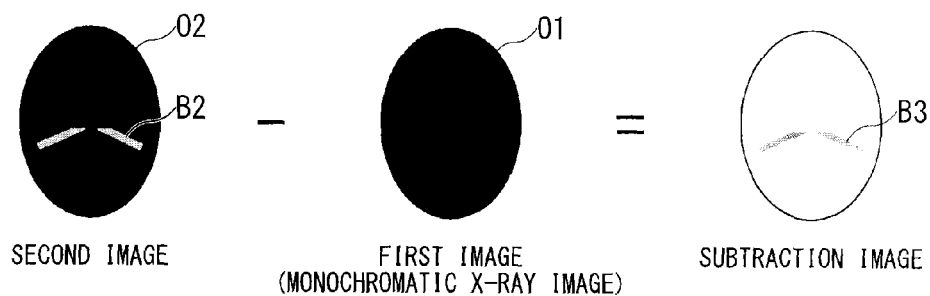
FIG. 8 is a diagram showing generation of a subtraction image.

FIG. 8 is a diagram showing generation of the subtraction image.

The leftmost of FIG. 8 shows the second image including a tissue O2 and a beam hardening artifact B2, the center shows the first image only including a tissue O1. The subtraction image at the rightmost of FIG. 8 includes a beam hardening artifact B3 having a CT value acquired by subtracting the CT value of the tissue O1 included in the first image from the CT value (luminance value) of the beam hardening artifact B2 included in the second image.

Figure 9:
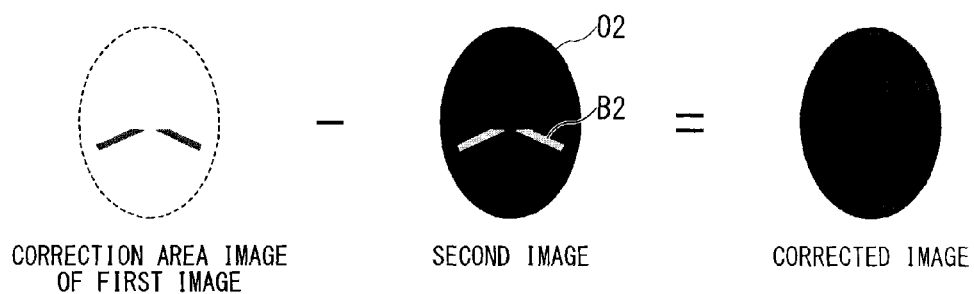
FIG. 9 is a diagram showing generation of a corrected image.

Returning to the description of FIG. 5, the correction area identifying 74d identifies an area to be corrected (correction area) in the first image read by the first image data reading 74a. The correction area identifying 74d thus identifies the area of beam hardening B3 (shown in FIG. 8) on the subtraction image generated by the subtraction image generating 74c, as the correction area in the first image. The leftmost of FIG. 9 shows a correction area image including the correction area.

The correction area identifying 74d is only required to extract an area having a difference of at least a certain threshold based on the subtraction process of the subtraction image generating 74c. In particular, the polychromatic X-ray blend image as the second image including the artifact fading to black may be sometimes improved by means of the monochromatic X-ray image. In this case, the artifact in the subtraction image has a minus value. Consequently, the correction area identifying 74d can extract the area of the artifact having a value smaller than the threshold. The correction area identifying 74d can therefore support removal of artifacts other than the beam hardening artifact.

The correcting 74e corrects the area identified by the correction area identifying 74d in the second image read by the second image data reading 74b on the basis of the first image. The correcting 74e generates the corrected image according to a combining process (superposition process) using the correction area image generated by the correction area identifying 74d on the basis of the first image (subtraction image) and the second image read by the second image data reading 74b, thereby correcting the second image.

For example, the correcting 74e aligns and combines (fuses) the correction area image itself and the second image itself with each other, thereby generating a corrected image as a display image. According to the display image, a beam hardening artifact B1 (shown in FIG. 8) appearing on the second image can be reduced. The correcting 74e may multiply one of the correction area image and the second image by a combining coefficient (weighting coefficient) w, and multiply the other by (1-w), thereby allowing the combining ratio to be changed.

FIG. 9 is a diagram showing generation of the corrected image.

FIG. 9 shows the corrected image acquired by combining the correction area image with the second image. According to the corrected image, the part of the beam hardening artifact B2 appearing on the second image is compensated with the first image. Consequently, no beam hardening artifact appears on the corrected image.

Subsequently, an operation of generating the display image in the X-ray CT apparatus 1 in the present embodiment is described.

Figure 10:
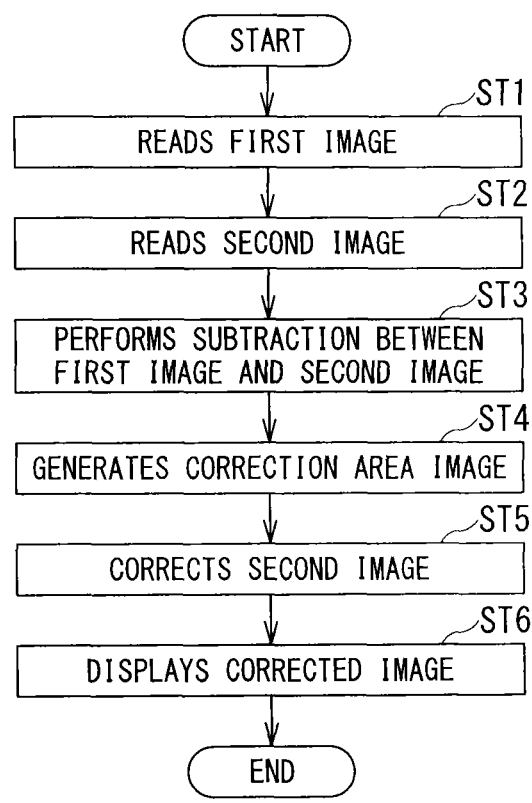
FIG. 10 is a flowchart showing an operation of generating a display image in the X-ray CT apparatus according to the present embodiment.

FIG. 10 is a flowchart showing the operation of generating the display image in the X-ray CT apparatus 1 according to the present embodiment.

The X-ray CT apparatus 1 reads, from the storage 63, the monochromatic X-ray image (or a polychromatic X-ray image taken at the relatively narrow X-ray energy band) taken at the required X-ray energy as the first image (step ST1). The X-ray CT apparatus 1 reads, as the second image, the polychromatic X-ray image taken at the relatively wide X-ray energy band (the image may be the polychromatic X-ray blend image) (step ST2).

The X-ray CT apparatus 1 performs subtraction between the first image read in step ST1 and the second image read in step ST2, thereby generating the subtraction image (step ST3). The X-ray CT apparatus 1 generates the correction area image that includes in the first image read in step ST1, the areas corresponding to the beam hardening B3 (shown in FIG. 8) as a correction target on the subtraction image generated in step ST3 (step ST4).

The X-ray CT apparatus 1 combines the correction area image generated in step ST4 with the second image read in step ST2, thereby generating the corrected image. The X-ray CT apparatus 1 then corrects the correction area in the second image on the basis of the subtraction image generated in step ST3 based on the first image (step ST5). The X-ray CT apparatus 1 displays the corrected image generated in step ST5 on the display 65 (step ST6).

(First Variation)

Figure 11:
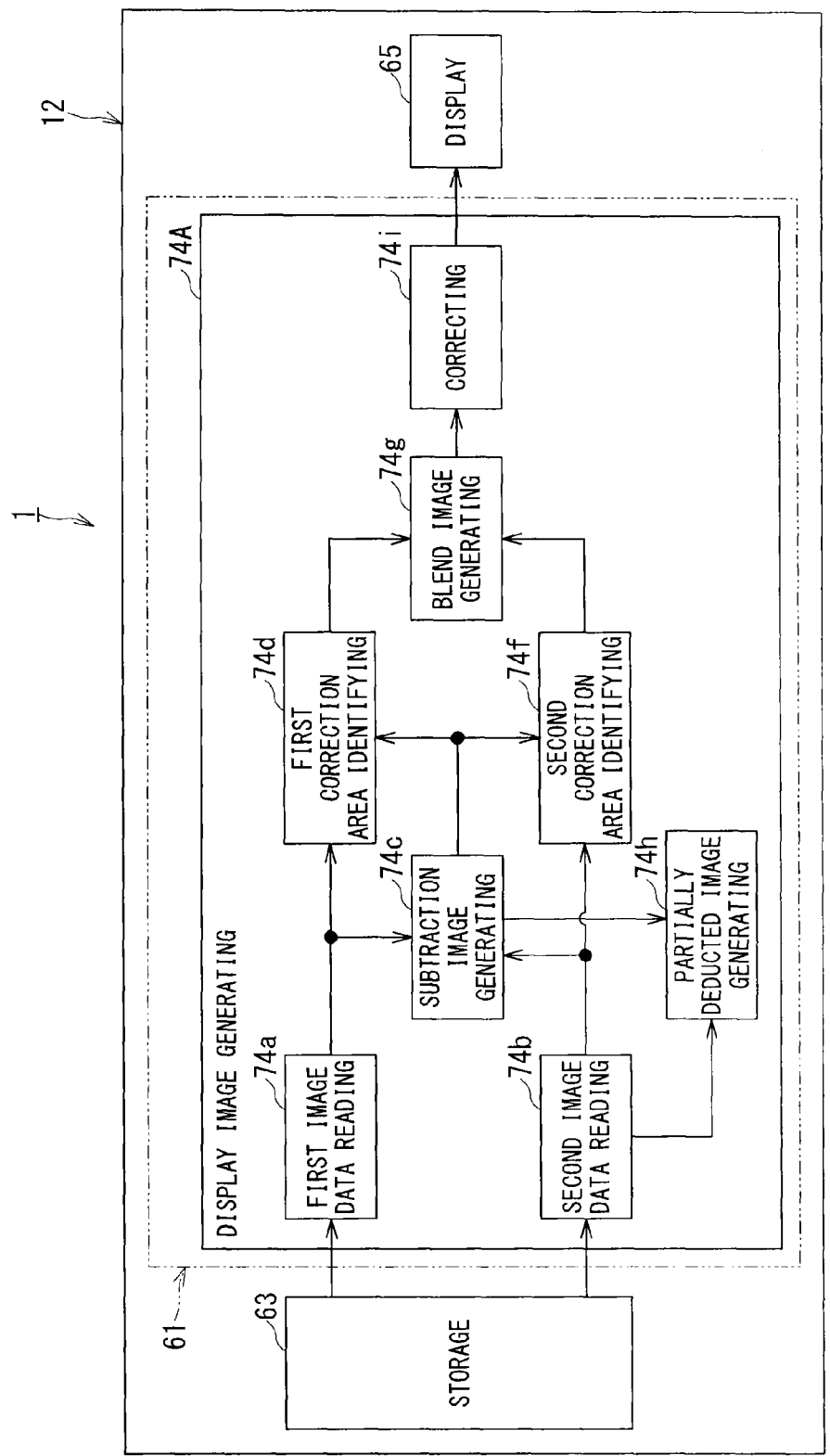
FIG. 11 is a block diagram showing functions of a first variation of the X-ray CT apparatus according to the present embodiment.
Figure 12:
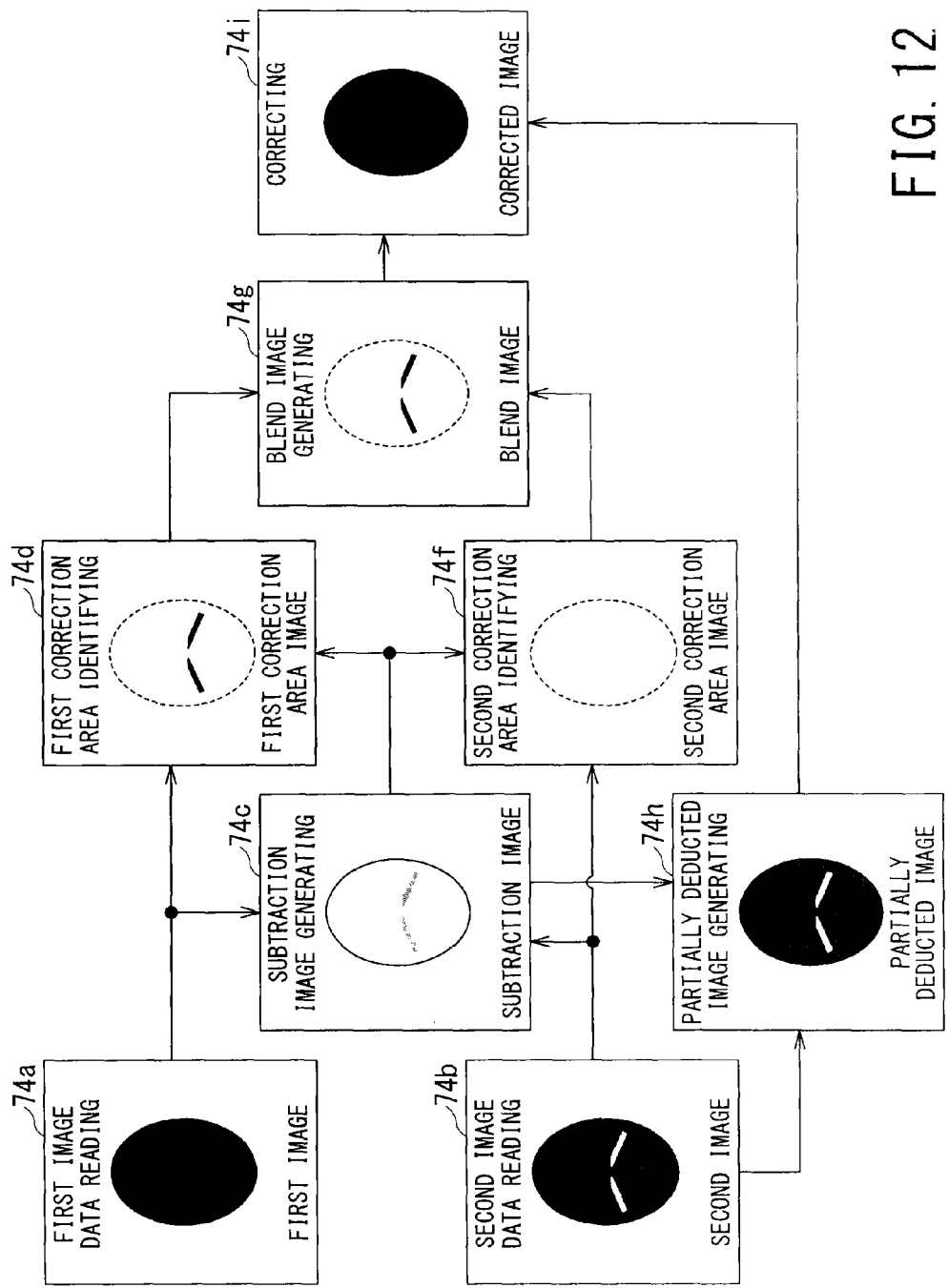
FIG. 12 is a diagram showing a flow of generating an image by the X-ray CT apparatus according to the first variation of the present embodiment.

FIG. 11 is a block diagram showing the functions of a first variation of the X-ray CT apparatus 1 according to the present embodiment. FIG. 11 shows a variation of FIG. 5. FIG. 12 is a diagram showing a flow of generating an image by the X-ray CT apparatus 1 according to the first variation of the present embodiment.

The processing circuitry 61 of the image processing apparatus 12 executes programs, thereby allowing the X-ray CT apparatus 1 to function as the tube voltage controlling 71, the first generating 72, the second generating 73, and a display image generating 74A as shown in FIGS. 4 and 11. All or some of the functions 71 to 74A are not necessarily included only in the image processing apparatus 12. Alternatively, these functions may be included in the high-voltage generator 55 or the controller 23.

The functions 71 to 74A may be configured as respective programs, thereby allowing a single processing circuit to execute the functions 71 to 74A. Alternatively, the functions 71 to 74A may be implemented in respective dedicated program executing circuits, which are independent from each other.

The display image generating 74A has a function of generating the display image, which is to be displayed, on the basis of the first image generated by the first generating 72 and the second image generated by the second generating 73. More specifically, the display image generating 74A includes a first image data reading 74a, a second image data reading 74b, a subtraction image generating 74c, a first correction area identifying (the correction area identifying shown in FIG. 5) 74d, a second correction area identifying 74f, a blend image generating 74g, a partially deducted image generating 74h, and a correcting 74i. The second image generated by the second generating 73 is any of the polychromatic X-ray image from the projection data set based on the single energy scan, the polychromatic X-ray image from the projection data set based on one mode of the dual energy scan, and the polychromatic X-ray blend image where the polychromatic X-ray images from the projection data sets based on the respective scans of the dual energy scan are blended (the lower part of FIG. 7).

In FIG. 11, the same symbols are assigned to the same components as those in FIG. 5, and description of these components are omitted.

The first correction area identifying 74d identifies a correction area, which is a correction target, in the first image read by the first image data reading 74a. The first correction area identifying 74d identifies, as the correction area, the area of the beam hardening B3 (shown in FIG. 8) on the subtraction image generated by the subtraction image generating 74c in the first image. For the identified correction area, a first correction area image is generated.

The second correction area identifying 74f identifies the area of the correction target in the second image read by the second image data reading 74b. The second correction area identifying 74f identifies the area of the beam hardening B3 (shown in FIG. 8) on the subtraction image generated by the subtraction image generating 74c in the second image. For the identified correction area, a second correction area image is generated.

The blend image generating 74g blends the first correction area image generated by the first correction area identifying 74d with the second correction area image generated by the second correction area identifying 74f, thereby generating the blend image. The blend image generating 74g performs a blending process according to a method similar to the method described with reference to the second image generating 73e (shown in FIG. 4). Any blending ratio may be freely set.

The partially deducted image generating 74h generates partially deducted image where the area of the beam hardening B3 (shown in FIG. 8) on the subtraction image generated by the subtraction image generating 74c is deducted from the second image read by the second image data reading 74b.

The correcting 74i generates the corrected image according to the combining process (superposition process) using the first correction area image (correction area image) generated by the first correction area identifying 74d and the second image read by the second image data reading 74b. For example, the correcting 74i generates the corrected image as the display image by aligning and combining (fusing) the blend image generated by the blend image generating 74g based on the first correction area image with the partially deducted image generated based on the second image, instead of the first correction area image itself or the second image itself.

According to the display image, the beam hardening artifact B1 (shown in FIG. 8) appearing on the second image can be reduced. The correcting 74i may multiply one of the blend image and the partially deducted image by the combining coefficient (weighting coefficient) w, and multiply the other by (1-w), thereby allowing the combining ratio to be changed.

The X-ray CT apparatus 1 of the present embodiment uses the first image to correct the area of the artifact in the second image whose noise is reduced, and generates an image to be displayed, thereby allowing the operator, such as a diagnostician, to be provided with a new image where both the artifact and noise are reduced. As a result, the X-ray CT apparatus 1 in the present embodiment improves the accuracy of image diagnosis.

(Second Variation)

Figure 13:
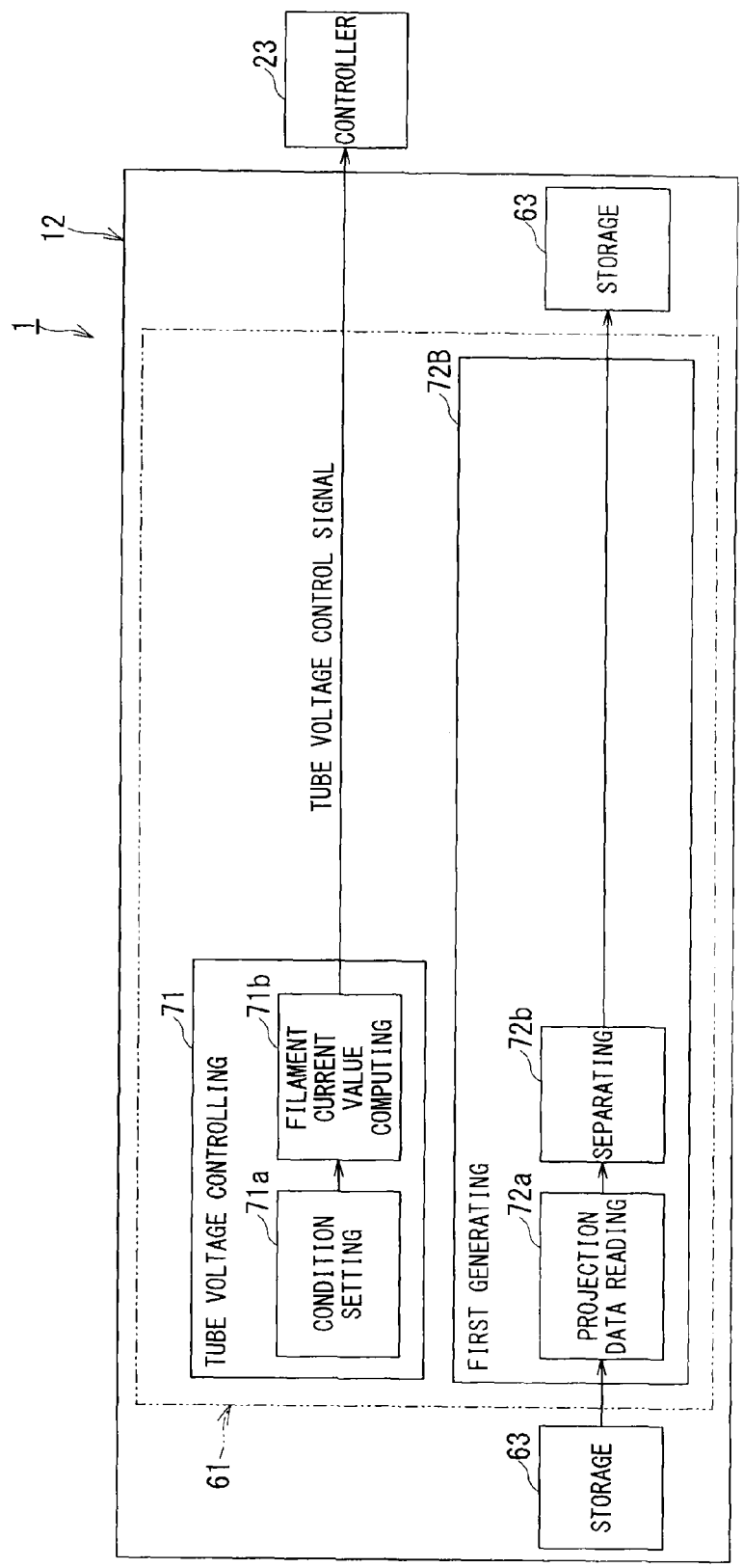
FIGS. 13 and 14 are block diagrams showing functions of a second variation of the X-ray CT apparatus according to the present embodiment.
Figure 14:
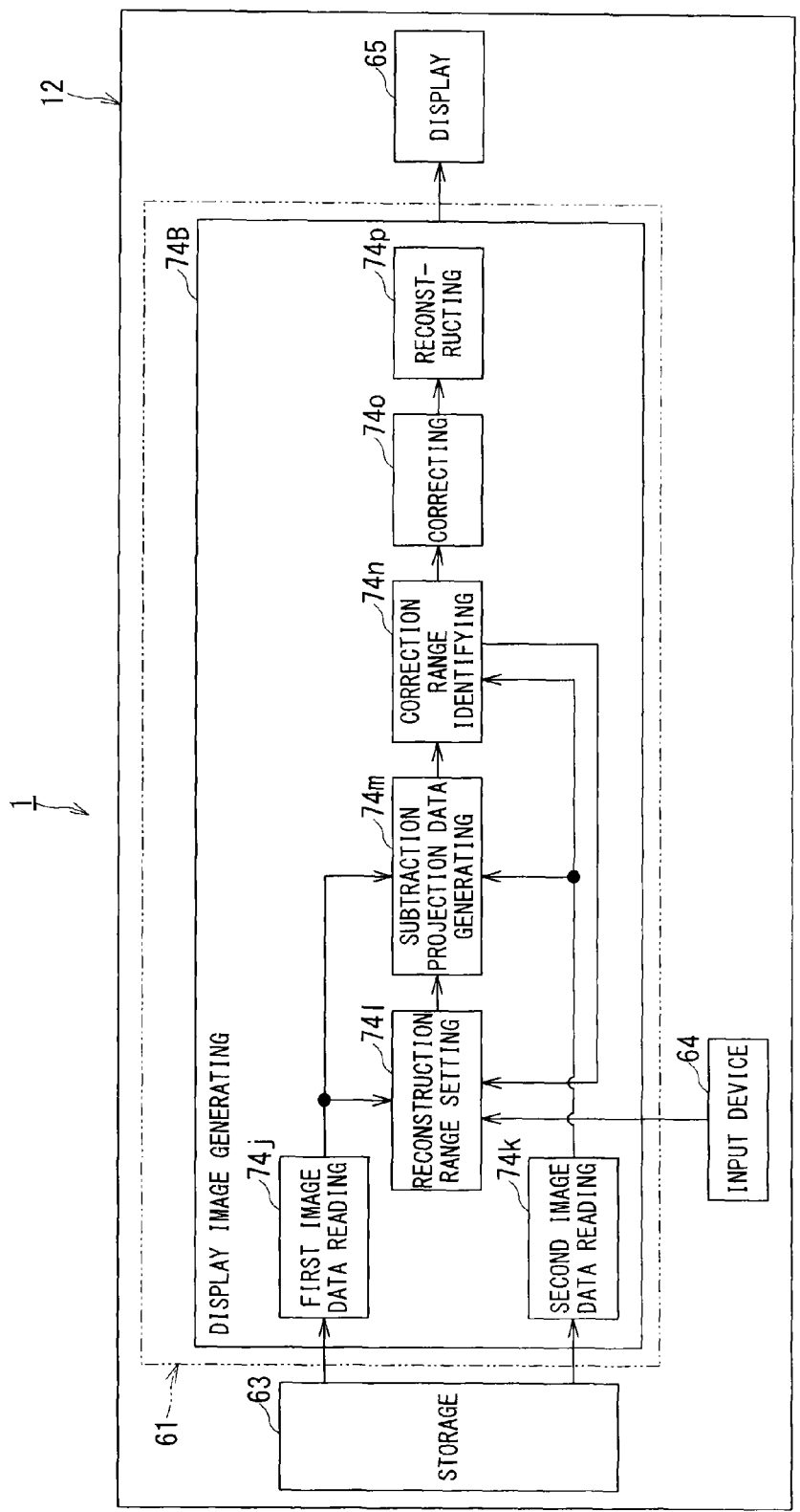

FIGS. 13 and 14 are block diagrams showing the functions of the X-ray CT apparatus 1 according to a second variation of the present embodiment. FIG. 13 shows a variation of FIG. 4. FIG. 14 shows a variation of FIG. 5.

FIGS. 4 and 5 show the configuration for the case of extracting a beam hardening component based on image data. Meanwhile, FIGS. 13 and 14 show the case of extracting the beam hardening component based on the pre-reconstruction data (projection data).

FIGS. 13 and 14 are block diagrams showing the functions of the second variation of the X-ray CT apparatus 1 according to the present embodiment.

The processing circuitry 61 of the image processing apparatus 12 executes programs, thereby allowing the X-ray CT apparatus 1 to function as a tube voltage controlling 71, a first generating 72B, and a display image generating 74B, as shown in FIGS. 13 and 14. All or some of the functions 71, 72B and 74B are not necessarily included only in the image processing apparatus 12. Alternatively, these functions may be included in the high-voltage generator 55 or the controller 23.

The functions 71, 72B and 74B may be configured as respective programs, thereby allowing a single processing circuit to execute the functions 71, 72B and 74B. Alternatively, the functions 71, 72B and 74B may be implemented in respective dedicated program executing circuits, which are independent from each other.

In FIGS. 13 and 14, the same symbols are assigned to the same components as those in FIGS. 4 and 5, and description of these components are omitted.

First, the first generating 72B shown in FIG. 13 is described.

The first generating 72B has a function of generating a first projection data set of monochromatic X-rays on the basis of two types of projection data sets acquired by the dual energy scan. Alternatively, the first generating 72B has a function of generating a first projection data set in a relatively narrow X-ray energy band on the basis of two types of projection data sets acquired by the dual energy scan. The present embodiment is described using the case where the first generating 72B generates the first projection data set of monochromatic X-rays.

More specifically, the first generating 72B functions as the projection data reading 72a and the separating 72b.

The separating 72b stores the projection data set of monochromatic X-rays as the first projection data set, in the storage 63.

Next, the display image generating 74B shown in FIG. 14 is described.

The display image generating 74B has a function of generating the display image to be displayed on the basis of the first projection data set generated by the first generating 72B and the projection data set (second projection data set) with polychromatic X-rays acquired by scanning in a second X-ray energy band that is wider than the first X-ray energy band. The display image generating 74B functions as a first projection data reading 74j, a second projection data reading 74k, a reconstruction range setting 74l, a subtraction projection data generating 74m, a correction range identifying 74n, a correcting 74o, and a reconstructing 74p.

The first projection data reading 74j reads the first projection data set that is generated by the first generating 72B and stored in the storage 63 of the image processing apparatus 12.

The second projection data reading 74k reads the second projection data set stored in the storage 63 of the image processing apparatus 12.

The reconstruction range setting 74l sets a range corresponding to a region of interest (ROI: region of interest) on a reconstructed image that is to be generated, as a reconstruction range on the first projection data set read by the first projection data reading 74j. It is only necessary that the reconstruction range is set on one first projection data item in the first projection data set and applied to another first projection data item. The reconstruction range may be set according to an instruction by the operator through the input device 64. Alternatively, a part of direct radiation of each first projection data item may be set as an automatically removed part. The reconstruction range setting 74l can reduce the load of reconstruction process by the reconstructing 74p.

The subtraction projection data generating 74m generates a subtraction projection data set by performing subtraction between the first projection data set read by the first projection data reading 74j and the second projection data set read by the second projection data reading 74k with respect to the projection data items of the same view. Alternatively, the subtraction projection data generating 74m generates the subtraction projection data set by performing subtraction between the reconstruction range of the first projection data set that is set by the reconstruction range setting 74l and the reconstruction range of the second projection data set with respect to the projection data items for each view. The present embodiment is described exemplifying the latter.

The subtraction projection data generating 74m performs subtraction between parts of the first projection data and the second projection data in the same view, the parts pertaining to the same detection element of the X-ray detector 53 (shown in FIG. 1).

The correction range identifying 74n identifies a range to be corrected in the reconstruction range in the first projection data set that is set by the reconstruction range setting 74l, as the correction range, on view-by-view basis. The correction range identifying 74n is only required to extract an area having at least a certain threshold based on the subtraction process of the subtraction projection data generating 74m.

The correcting 74o corrects the correction range identified by the correction range identifying 74n in the second projection data set that is set by the reconstruction range setting 74l, on the basis of the first projection data set, on view-by-view basis. The correcting 74o corrects the second projection data set by generating the corrected projection data set through the combining process (addition, addition and averaging, and weighted averaging processes) using the correction range set by the correction range identifying 74n on the basis of each first projection data item (subtraction projection data item) and each second projection data item.

Here, the reconstruction range setting 74l, the subtraction projection data generating 74m, the correction range identifying 74n, and the correcting 74o can correct the correction range of all the second projection data items included in the second projection data set. Alternatively, the reconstruction range setting 74l, the subtraction projection data generating 74m, the correction range identifying 74n, and the correcting 74o may thin out some second projection data items included in the second projection data set and correct the correction range only for another second projection data item.

The reconstructing 74p generates the corrected image as the display image on the basis of the corrected projection data set generated by the correcting 74o.

According to the display image, the beam hardening artifacts appearing on the image based on the second projection data set (polychromatic X-ray projection data set) can be reduced.

Here, in some cases, the display image is generated by the reconstructing 74p, and subsequently the region of interest (ROI) set on the display image is reconstructed (enlarged and reconstructed) again. In such cases, the reconstruction range setting 74l can set the range corresponding to the region of interest on the display image as the reconstruction range, on the first projection data set read by the first projection data reading 74j. The reconstruction range setting 74l can reduce the load of the reconstruction process to be executed again by the reconstructing 74p.

The X-ray CT apparatus 1 according to the second variation of the present embodiment can provide the operator, such as the diagnostician, with a new image with both artifacts and noise being reduced, by correcting the range of the artifact in the second projection data set (polychromatic X-ray projection data set) with reduced noise using the first projection data set (projection data set of monochromatic X-rays) and generating the image to be displayed. As a result, the X-ray CT apparatus 1 of the present embodiment can improve the accuracy of image diagnosis.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
an X-ray tube configured to emit X-rays;
a high-voltage power supply configured to apply a tube voltage to the X-ray tube;
an X-ray detector including a plurality of X-ray detection elements, and configured to detect the X-rays; and
a processing circuitry configured to:
reconstruct, as a first image, any of a monochromatic X-ray image and a polychromatic X-ray image on a basis of pre-reconstruction data acquired by scanning an object, the polychromatic X-ray image being taken in a first X-ray energy band;
reconstruct, as a second image, a polychromatic X-ray image taken in a second X-ray energy band wider than the first X-ray energy band on a basis of a pre-reconstruction data acquired by scanning the object;
identify an area of a correction target in the first image as a correction area; and
correct the correction area in the second image on a basis of the first image.

2. The X-ray CT apparatus according to claim 1, wherein the processing circuitry is configured to generate the first image from multiple types of the pre-reconstruction data based on a multi-energy scan.

3. The X-ray CT apparatus according to claim 1, wherein the processing circuitry is configured to adopt the second image that is any of the polychromatic X-ray image based on a single energy scan, the polychromatic X-ray image based on one mode of a multi-energy scan, and the polychromatic X-ray image where polychromatic X-ray image elements based on respective modes of the multi-energy scan are blended together.

4. An X-ray CT apparatus, comprising:
an X-ray tube configured to emit X-rays;
a high-voltage power supply configured to apply a tube voltage to the X-ray tube;
an X-ray detector including a plurality of X-ray detection elements, and configured to detect the X-rays; and
a processing circuitry configured to:
generate, as first pre-reconstruction data, any of pre-reconstruction data with monochromatic X-rays, and pre-reconstruction data with polychromatic X-rays on a basis of pre-reconstruction data acquired by scanning an object, the pre-reconstruction data being in a first X-ray energy band;
identify a range of a correction target as a correction range in the first pre-reconstruction data on a basis of the first pre-reconstruction data and a second pre-reconstruction data with polychromatic X-rays, the second pre-reconstruction data being acquired by scanning the object and being in a second X-ray energy band wider than the first X-ray energy band;
correct the correction range in the second pre-reconstruction data on a basis of the first pre-reconstruction data; and
reconstruct a corrected image on a basis of the corrected second pre-reconstruction data.

5. The X-ray CT apparatus according to claim 4, wherein the processing circuitry is configured to:
generate subtraction pre-reconstruction data by performing subtraction between the first pre-reconstruction data and the second pre-reconstruction data; and
generate the corrected second pre-reconstruction data using the subtraction pre-reconstruction data and the second pre-reconstruction data.

6. The X-ray CT apparatus according to claim 4, wherein the processing circuitry is configured to:
set a reconstruction range in the first pre-reconstruction data, and generate subtraction pre-reconstruction data by performing subtraction between the reconstruction range of the first pre-reconstruction data and the second pre-reconstruction data; and
generate the corrected second pre-reconstruction data using the subtraction pre-reconstruction data and the second pre-reconstruction data.

7. An image processing apparatus, comprising:
a processing circuitry and a memory, wherein
the processing circuitry is configured to:
reconstruct, as a first image, any of a monochromatic X-ray image and a polychromatic X-ray image on a basis of pre-reconstruction data acquired by an X-ray detector detecting X-rays having been emitted by an X-ray tube and transmitted through an object, the polychromatic X-ray image being taken in a first X-ray energy band;
reconstruct, as a second image, a polychromatic X-ray image taken in a second X-ray energy band wider than the first X-ray energy band on a basis of a pre-reconstruction data;
identify an area of a correction target in the first image as a correction area; and
correct the correction area in the second image on a basis of the first image.

8. The image processing apparatus according to claim 7, wherein
the processing circuitry is configured to generate the first image from multiple types of the pre-reconstruction data based on a multi-energy scan.

9. The image processing apparatus according to claim 7, wherein
the processing circuitry is configured to adopt the second image that is any of the polychromatic X-ray image based on a single energy scan, the polychromatic X-ray image based on one mode of a multi-energy scan, and the polychromatic X-ray image where polychromatic X-ray image elements based on respective modes of the multi-energy scan are blended together.

10. The image processing apparatus according to claim 7, wherein
the processing circuitry is configured to:
generate a subtraction image by performing subtraction between the first image and the second image; and generate a corrected image using the subtraction image and the second image.

11. The image processing apparatus according to claim 10, wherein
the processing circuitry is configured to:
generate a correction area image including a partial area of the subtraction image in the first image; and
generate the corrected image by aligning and combining the correction area image and the second image with each other.

12. The image processing apparatus according to claim 11, wherein
the processing circuitry is configured to change a combining ratio between the correction area image and the second image.

13. The image processing apparatus according to claim 11, wherein
the processing circuitry is configured to:
generate a first correction area image that is a part of the first image including a partial area in the subtraction image;
generate a second correction area image where only the partial area in the subtraction image is extracted from the second image;
generate a blend image by blending the first correction area image and the second correction area image;
generate a partially deducted image that is the second image from which the partial area of the subtraction image is deducted; and
generate the corrected image by aligning and combining the blend image and the partially deducted image with each other.

14. The image processing apparatus according to claim 13, wherein
the processing circuitry is configured to change a combining ratio between the blend image and the partially deducted image.

15. The image processing apparatus according to claim 7, wherein
the processing circuitry is configured to perform subtraction between the first image and the second image having CT values closest to each other, if the second image is a polychromatic X-ray image where polychromatic X-ray image elements based on respective modes of a multi-energy scan are blended together.

16. An image processing apparatus, comprising:
a processing circuitry and a memory, wherein
the processing circuitry is configured to:
generate, as first pre-reconstruction data, any of pre-reconstruction data with monochromatic X-rays, and pre-reconstruction data with polychromatic X-rays on a basis of pre-reconstruction data acquired by scanning an object with an X-ray CT apparatus, the pre-reconstruction data being in a first X-ray energy band;
identify a range of a correction target as a correction range in the first pre-reconstruction data on a basis of the first pre-reconstruction data and a second pre-reconstruction data with polychromatic X-rays, the second pre-reconstruction data being acquired by scanning the object and being in a second X-ray energy band wider than the first X-ray energy band;
correct the correction range in the second pre-reconstruction data on a basis of the first pre-reconstruction data; and
reconstruct a corrected image on a basis of the corrected second pre-reconstruction data.

17. The image processing apparatus according to claim 16, wherein
the processing circuitry is configured to:
generate subtraction pre-reconstruction data by performing subtraction between the first pre-reconstruction data and the second pre-reconstruction data; and
generate the corrected second pre-reconstruction data using the subtraction pre-reconstruction data and the second pre-reconstruction data.

18. The image processing apparatus according to claim 16, wherein
the processing circuitry is configured to:
set a reconstruction range in the first pre-reconstruction data, and generate subtraction pre-reconstruction data by performing subtraction between the reconstruction range of the first pre-reconstruction data and the second pre-reconstruction data; and
generate the corrected second pre-reconstruction data using the subtraction pre-reconstruction data and the second pre-reconstruction data.

* * * * *